(12) United States Patent
Nikanorov et al.

(10) Patent No.: US 11,090,174 B1
(45) Date of Patent: Aug. 17, 2021

(54) TEMPORARY AND RETRIEVABLE EXPANDABLE MEMBER

(71) Applicant: Amaitus, Inc., Palo Alto, CA (US)

(72) Inventors: Alexander Nikanorov, Palo Alto, CA (US); Hugh Qinghong Zhao, Pleasanton, CA (US)

(73) Assignee: Amaitus, Inc., Palo Alto, CA (US)

( * ) Notice: Subject to any disclaimer, the term of this patent is extended or adjusted under 35 U.S.C. 154(b) by 0 days.

(21) Appl. No.: 16/787,573

(22) Filed: Feb. 11, 2020

(51) Int. Cl.
*A61F 2/88* (2006.01)

(52) U.S. Cl.
CPC ........ *A61F 2/88* (2013.01); *A61F 2250/0059* (2013.01)

(58) Field of Classification Search
CPC .... A61F 2/013; A61F 2/88; A61F 2230/0093; A61F 2230/0067; A61F 2002/016; A61B 17/221; A61B 17/22031; A61B 2017/2212; A61B 2017/2215; A61B 2017/2217; A61B 2017/22034; A61B 2017/22035; A61B 2250/0059
See application file for complete search history.

(56) References Cited

U.S. PATENT DOCUMENTS

| | | | | |
|---|---|---|---|---|
| 4,921,484 A | * | 5/1990 | Hillstead | A61M 25/10 604/104 |
| 4,998,539 A | * | 3/1991 | Delsanti | A61F 2/90 128/898 |
| 5,015,253 A | * | 5/1991 | MacGregor | A61F 2/88 623/1.15 |
| 5,061,275 A | * | 10/1991 | Wallsten | D04C 1/06 623/1.22 |
| 5,222,971 A | | 6/1993 | Willard et al. | |
| 5,476,508 A | * | 12/1995 | Amstrup | A61F 2/90 606/191 |
| 5,972,019 A | | 10/1999 | Engelson et al. | |
| 6,238,412 B1 | * | 5/2001 | Dubrul | A61B 17/22 606/108 |
| 6,635,068 B1 | * | 10/2003 | Dubrul | A61B 17/12022 606/200 |

(Continued)

OTHER PUBLICATIONS

"International Application Serial No. PCT/US2020/054546, International Search Report dated Jan. 8, 2021", 2 pgs.

(Continued)

*Primary Examiner* — Dianne Dornbusch
(74) *Attorney, Agent, or Firm* — Schwegman Lundberg & Woessner, P.A.

(57) ABSTRACT

A temporary expandable tissue support device includes a plurality of helical filaments superimposed on top of one another to form a tubular body. A first end of the tubular body is coupled to an inner shaft, and a second end of the tubular body is coupled to an outer shaft slidably disposed over the inner shaft. Actuation of the inner and outer shafts in a first direction compresses the plurality of filaments thereby radially expanding the tubular body into an expanded configuration adapted to engage and support tissue at a treatment site without obstructing a fluid from flowing past the tubular body. Actuation of the shafts in a second direction opposite the first direction tensions the plurality of filaments thereby radially collapsing the tubular body into a collapsed configuration that is adapted to be delivered to or removed from the treatment site.

8 Claims, 16 Drawing Sheets

(56) References Cited

U.S. PATENT DOCUMENTS

| | | | |
|---|---|---|---|
| 7,323,001 B2* | 1/2008 | Clubb | A61F 2/01 |
| | | | 606/200 |
| 10,779,852 B2* | 9/2020 | Bruzzi | A61B 17/32056 |
| 2004/0122466 A1 | 6/2004 | Bales | |
| 2004/0260333 A1* | 12/2004 | Dubrul | A61M 25/0119 |
| | | | 606/200 |
| 2005/0021075 A1* | 1/2005 | Bonnette | A61F 2/013 |
| | | | 606/200 |
| 2005/0149159 A1 | 7/2005 | Andreas et al. | |
| 2005/0283186 A1* | 12/2005 | Berrada | A61F 2/013 |
| | | | 606/200 |
| 2007/0225789 A1 | 9/2007 | Kavanagh et al. | |
| 2009/0264988 A1 | 10/2009 | Mafi et al. | |
| 2011/0224707 A1* | 9/2011 | Miloslavski | A61B 17/221 |
| | | | 606/159 |
| 2014/0343585 A1 | 11/2014 | Ferrera et al. | |
| 2016/0038174 A1* | 2/2016 | Bruzzi | A61B 17/320758 |
| | | | 606/159 |
| 2016/0192956 A1* | 7/2016 | Brady | A61B 17/22031 |
| | | | 606/159 |
| 2016/0206344 A1* | 7/2016 | Bruzzi | A61B 17/320783 |
| 2016/0256304 A1 | 9/2016 | Roeder et al. | |
| 2019/0254846 A1 | 8/2019 | Gianotti et al. | |

OTHER PUBLICATIONS

"International Application Serial No. PCT/US2020/054546, Written Opinion dated Jan. 8, 2012", 8 pgs.

* cited by examiner

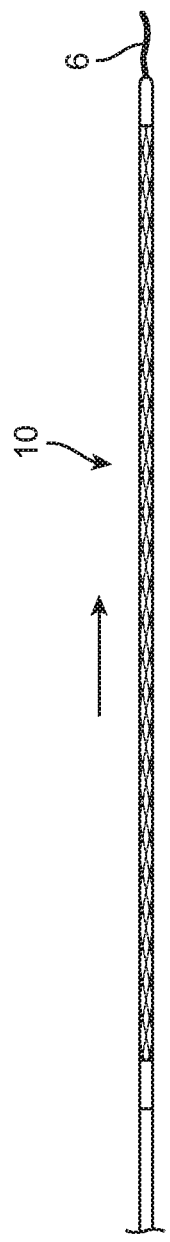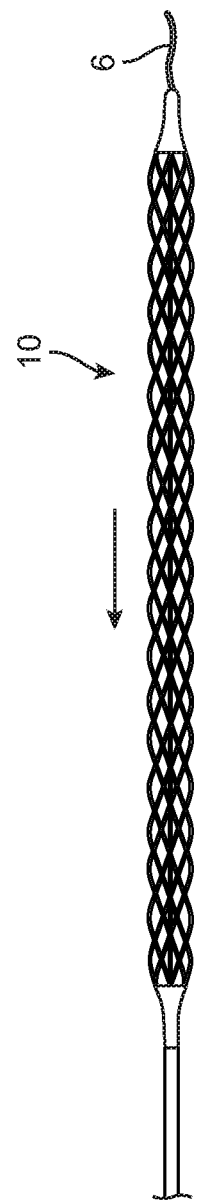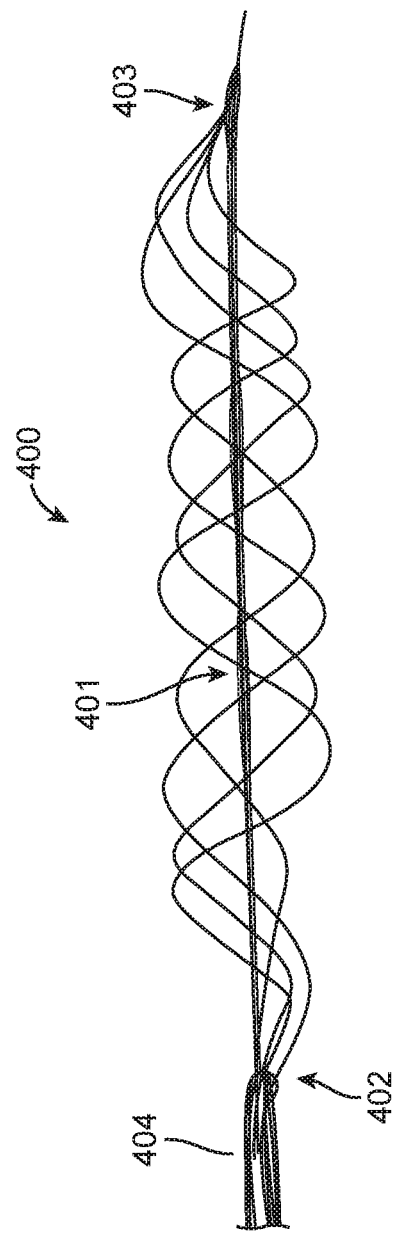
FIG. 3A
FIG. 3B
FIG. 4A

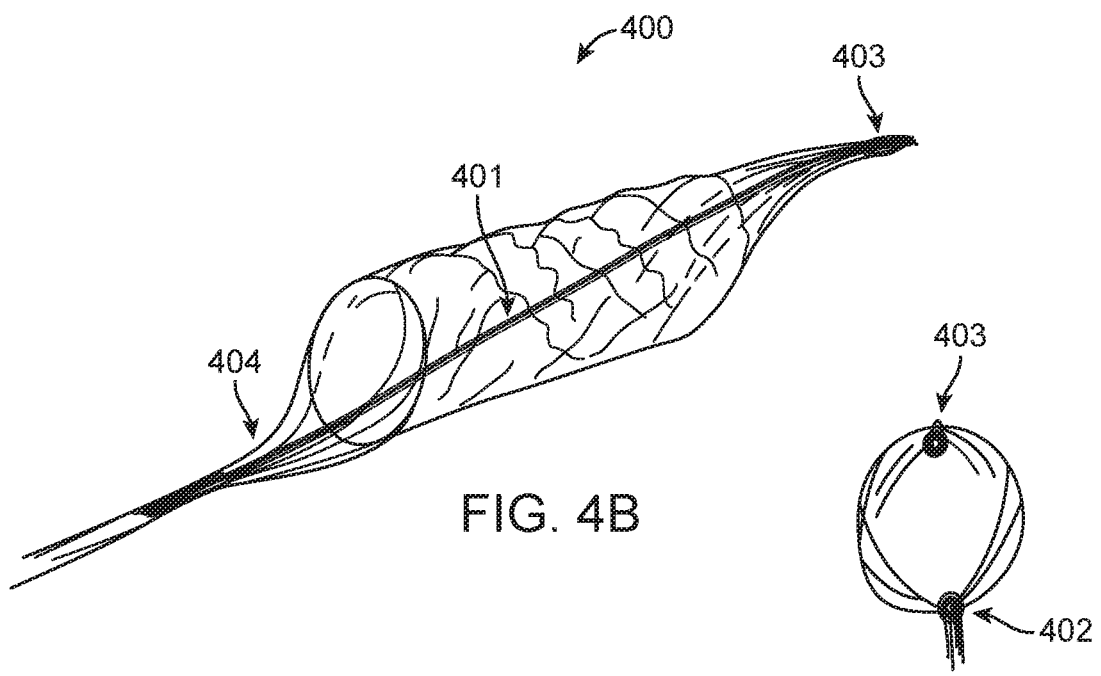
FIG. 4B
FIG. 4C
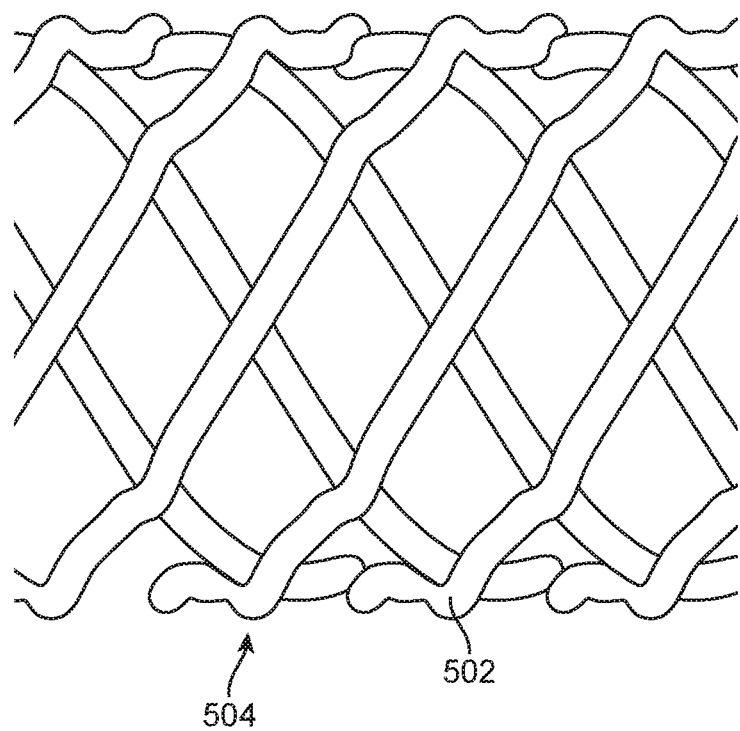
FIG. 5A

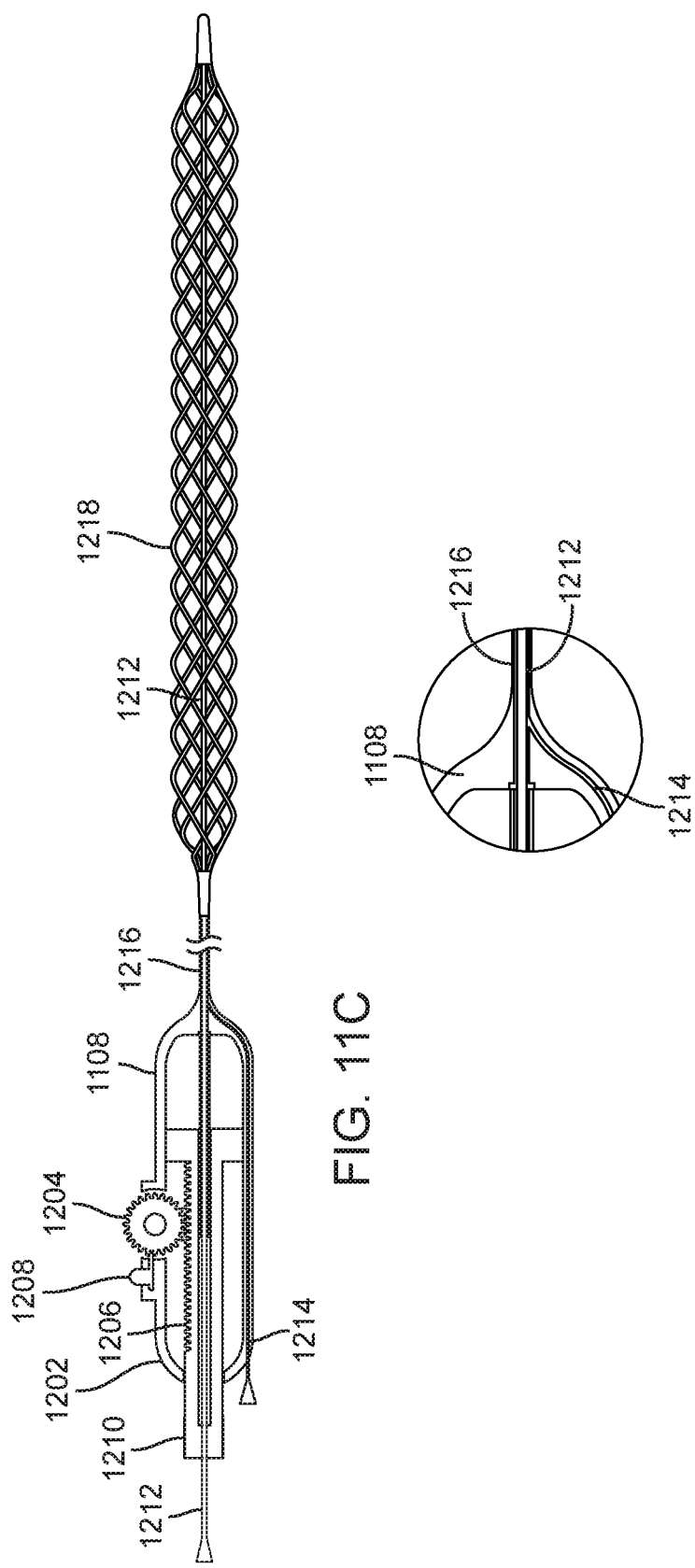

TEMPORARY AND RETRIEVABLE EXPANDABLE MEMBER

CLAIM OF PRIORITY

N/A

CROSS-REFERENCE TO RELATED PATENT DOCUMENTS

N/A

BACKGROUND

Narrowing or occlusion of body lumens or other passageways are a common medical condition, specifically in the blood vessels (e.g. arteries and veins) and airways (e.g. nasal passageway, sinuses, trachea, bronchi, etc.). Other examples include but are not limited to peripheral artery disease (PAD) including the superficial femoral artery (SFA), popliteal artery, vessels above or below the knee (A/K or BTK), iliac artery, aorta, renal arteries, coronary artery disease (CAD), and heart valves, etc. Treatment options may include one or more of bare metal stents, drug eluting stents, absorbable stents, plain old balloon angioplasty (POBA), drug coated balloons (DCB), open surgery, and other treatments known in the art.

Coronary artery disease (CAD) also referred to as coronary heart disease (CHD) is the most common type of heart disease, killing over 370,000 people annually. Every year about 735,000 Americans have a heart attack. Of these, 525,000 are a first heart attack and 210,000 happen in people who have already had a heart attack. Current treatments include but are not limited to stenting, POBA, etc.

In the case of PAD, an estimated 200 million patients worldwide suffer from this condition, including 20 million patients in the USA. PAD has a five-year mortality rate of about 30% and is estimated to cost the US healthcare system approximately $319 billion annually. The average cost to treat a Medicare beneficiary was over $11,000 per patient in 2015 as compared to the average PAD patient cost of over $72,000.

Obstruction or blockages of lumens or other body channels is not limited to the vascular system and may include other lumen occlusions and obstructions such as the trachea, nasal passageways, or any other lumen or body channel where fluids such as a gas or liquid pass through.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 3A and 3B illustrate the radially expandable member of FIG. 1 in the collapsed and expanded configurations, respectively.

FIG. 4A shows a side view of an asymmetrical radially expandable member.

FIG. 4B shows a perspective view of the radially expandable member in FIG. 4A.

FIG. 4C shows and end view of the radially expandable member in FIG. 4A.

FIG. 5A shows side view of an example of the helical filaments in a radially expandable member in the expanded configuration.

FIG. 11C illustrates an example of a handle with an actuator coupled to an expandable member.

FIG. 11D highlights a distal region of the handle in FIG. 11C.

DETAILED DESCRIPTION

Narrowing or occlusion of body lumens are a common medical condition, specifically in the blood vessels (e.g. arteries and veins) and airways (e.g. nasal passageway, sinuses, trachea, bronchi, etc.). Other examples include but are not limited to Peripheral artery disease (PAD) including the superficial femoral artery (SFA), popliteal artery, vessels above or below the knee (A/K or BTK), iliac artery, aorta, renal arteries, coronary artery disease (CAD), heart valves, etc. Treatment options may include one or more of bare metal stents, drug eluting stents, absorbable stents, plain old balloon angioplasty (POBA), drug coated balloons (DCB), open surgery, and other treatments known in the art.

Obstruction or blockages of body channels is not limited to the vascular system and may include other lumen occlusions and obstructions including the trachea, nasal passageways, or any other lumen or body channel where fluids such as a gas or a liquid pass through.

Each of these treatments have their advantages and disadvantages. It would be desirable to provide improved devices, methods, and systems for treating at least some of these diseases.

The examples disclosed herein generally relate to the field of medical devices, systems, and methods. More particularly, the devices, systems and methods are described in relation to intraluminal devices such as endovascular, intraarterial, intravenous, endolymphatic, endotracheal, endobronchial, nasal, sinusoidal, ductal, ureteral) support scaffold-like devices for temporary placement and removal. Other applicable devices, systems and methods may be related to lumen wall support and medicinal delivery that can perform the functions of repeated expanding and collapsing, and so that the device can be delivered upon radially collapsing into a lower profile that can be delivered to a targeted anatomy and/or lesions, then radially expanded to support the lumen opening for a desirable period of time, repositioned upon radially collapsing and re-expanding, and then retrieved upon re-collapsing, and its preparation method and use thereof. These examples are of course not intended to be limiting and one of skill in the art will appreciate that the devices, systems, and methods disclosed herein may be used in many other applications.

Figure 1:
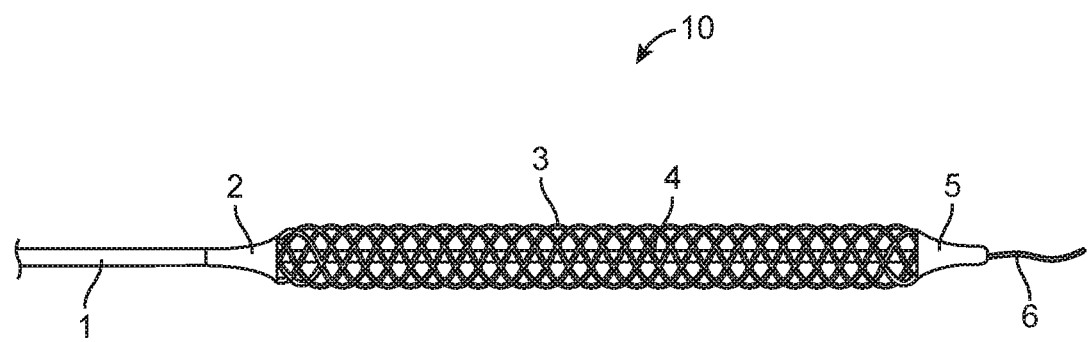
FIG. 1 illustrates an example of a radially expandable member.

FIG. 1 shows an example of a scaffold-like device 10 formed from a plurality of superimposed helical filaments 3 such as wires. FIG. 1 shows the device 10 in the expanded state and includes an outer shaft 1, a proximal portion of the device 2 with the outer shaft 1 (also referred to as outer tube) coupled to the proximal portion of helical filaments 3. Inner shaft 4 is disposed under the expandable tubular body formed by the helical filaments and may be coaxially disposed under the expandable tubular body. The distal portion of the helical filaments is coupled to a distal portion of the inner shaft to form a distal joint 5. An optional guidewire 6 may be disposed through a lumen in the inner shaft 4, and the inner shaft may extend slidably through a lumen in the outer shaft 1. The helical filaments form a hollow tubular body with apertures in the sidewall which allow fluids such as a gas like air, or a fluid like blood to flow through the device when it is collapsed and being delivered, or when it is expanded and engaged with the walls of the lumen or other treatment site. An outer layer of heat shrink tubing may be applied at the proximal and distal ends of the tubular body where the filaments are coupled to the inner and outer shafts to provide a smoother, atraumatic surface at the proximal and distal ends.

The scaffold-like design uses superimposed helical wires having distal ends joined with the tip of an inner shaft (also referred to herein as an inner member) such as a hypotube, and the proximal ends of the helical wires are joined to an outer shaft (also referred to herein as an outer member) such as sheath. The superimposed helical scaffold-like device may be fabricated from any type of filament such as thin wires or threads with any diameter, including a diameter ranging from 50 to 500 microns, although any size may be used. The outer shaft may be made of a thin-walled tube with good resistance to kinking. The inner shaft may be made of a hypotube or any other material that can be slidably passed through the lumen of outer member. The diameter of the inner tube may range from 150 to 1500 microns, although this is not intended to be limiting. Relative movement of the inner shaft and outer shaft will actuate the plurality of filaments to either expand or collapse the tubular body formed by the filaments, as will be discussed in greater detail below.

Figure 2:
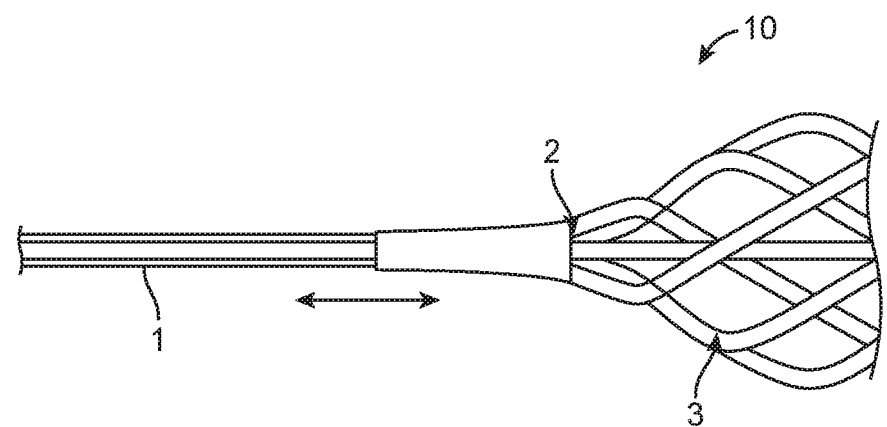
FIG. 2 illustrates a proximal portion of the radially expandable member in FIG. 1.

FIG. 2 illustrates a close-up of the proximal portion of the expandable device 10 illustrated in FIG. 1 above where the joint is formed using techniques known in the art such as adhesive bonding, welding, or other methods. The proximal portion 2 of superimposed helical wires 3 are fixed onto the end portion of the outer shaft 1, and an inner member slides inside a lumen of the outer shaft via a distal pushing or a proximal pulling motion as indicated by the arrow, passing under the helical filaments. At the proximal joint, the helical wires are welded, bonded, or otherwise fixedly coupled to the outside surface of the outer member which may have a wall thickness ranging from 100 to 500 microns, although this is not intended to be limiting. The number of superimposed helical wires may range from 2 to 12 depending on the helix pattern, although this is not intended to limit the number of filaments used. An outer heat shrink tubing or other sleeve may be disposed over the proximal end of the plurality of filaments to provide a smooth transition from the outer shaft to the filament region. The distal joint may be similarly formed or may be formed using other techniques known in the art.

FIGS. 3A and 3B illustrate the expandable member 10 of FIG. 1 in the collapsed and expanded configurations, respectively. Optional guidewire 6 is also show extending from the inner shaft. The superimposed helical scaffold-like device may be radially expanded by moving the inner shaft relative to the outer shaft, for example by pulling the inner movable shaft proximally into the outer stable shaft as illustrated by the arrow in FIG. 3B. This applies compression to the plurality of helical filaments which then bow radially outward to radially expand and form the tubular body. Continued movement of the inner shaft relative to the outer shaft will further increase the diameter of the tubular body until a maximum diameter is obtained. Additionally, with increased diameter, the tubular body will exert higher radial force as it engages and supports tissue. Since relative motion is required to actuate the expandable member, a similar result may be obtained by pushing the outer shaft over the inner shaft to compress and expand the filaments, or a combination of pushing and pulling the inner and outer shafts relative to one another may also be used to expand the filaments into the tubular body.

Actuation of the inner and outer shafts relative to one another in the opposite direction as required to expand the device will also radially collapse the expanded tubular body and reduce the applied radial force when the compression on the helical filaments is released and tension is applied to the helical filaments. For example, the inner shaft may be advanced distally relative to the outer shaft as indicated by the arrow in FIG. 3A, or the outer shaft may be retracted proximally relative to the inner shaft, or a combination of both motions may be used to remove the compression on the filaments thereby radially collapsing the tubular body into the collapsed configuration. The collapsed configuration has a small enough profile to permit delivery to the target treatment area (e.g. through a blood vessel lumen or another body channel). The diameter of the expanded device is determined by the geometry of the superimposed helical structure and may be any diameter, including but not limited to a diameter ranging from 2 to 35 millimeters. Similarly, the profile of the collapsed device maybe any size, including but not limited to 1.4 mm to 3.2 mm in diameter.

Thus, the tubular body may be expanded or collapsed to any size and provide any desired radial force from the fully collapsed configuration to the full expanded configuration and positions in between. Additionally, the device may expanded and collapsed multiple times without fatiguing.

FIG. 4A shows an expandable scaffold 400 which may be any of the examples disclosed herein but with the proximal and distal ends of the filaments coupled to the inner 401 and outer shafts 404 asymmetrically. For example, in the example of FIG. 1, the helical filaments may be evenly distributed circumferentially around the inner and outer shafts to form a symmetrical cylindrical tube when expanded. However, in FIG. 4A, the distal ends of the filaments are coupled to an upper portion 403 of the inner shaft while the lower portion of the inner shaft is free of helical filaments. The proximal ends of the filaments are coupled to a lower portion 402 of the outer shaft while the upper portion of the outer shaft is free of filaments. The proximal and distal ends of the filaments may be offset any amount, but in FIG. 4A, the ends are offset approximately 180 degrees circumferentially from one another relative to the longitudinal axis of the inner and outer coaxial shafts. The middle section of the helical filaments between the proximal and distal filament ends may be evenly distributed around the inner and outer shafts to form a tubular body.

FIG. 4B shows the expanded tubular body formed when the example of FIG. 4A is radially expanded. The tubular body has a central portion that is substantially a cylindrical tube symmetric in shape, while the distal end has a distally tapering pointed end and the wall of the tubular body tapers from a full closed cylindrical wall to a partial open wall that tapers down to a point where the filaments are coupled to the inner shaft 401. And similarly, the proximal end also tapers proximally down from a full cylindrical closed wall to a partial open wall that tapers down to a point where the filaments are coupled to the outer shaft 404. This may also be described as the partially open wall flaring distally to the fully closed cylindrical wall. In this example, the proximal and distal coupling points are offset approximately 180 degrees from one another. The tapered proximal and distal open walls are pointed protrusions that are offset by approximately 180 degrees from one another. Any offset may be established by adjusting the proximal and distal connection points of the filaments to the inner and outer shafts.

FIG. 4C shows the proximal and distal connection points where the helical filaments are coupled to the inner shaft and the outer shaft circumferentially offset from one another by approximately 180 degrees, although this is not intended to be limiting and the offset may be set to any value between 0 and 360 degrees relative to the first connection point.

Figure 5B:
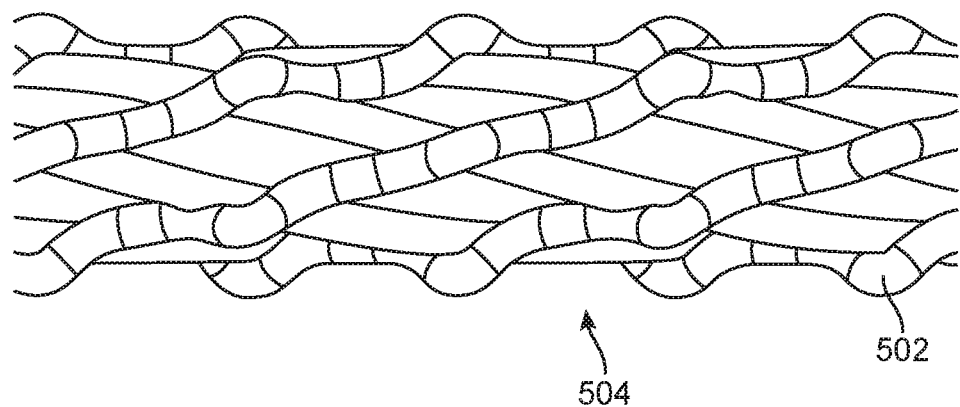
FIG. 5B shows a side view the radially expandable member of FIG. 5A in the collapsed configuration.

FIGS. 5A-5D illustrate various examples of superimposed helical filaments 502. FIG. 5A shows the tubular body 504 formed by the superimposed helical filaments 502 in an expanded configuration, and FIG. 5B shows the tubular body of FIG. 5A in the collapsed configuration. In FIG. 5A the tubular body is formed from a plurality of superimposed helical filaments. At no position are there more than two filaments, so there is an inner-most layer of filaments and an outer-most layer of filaments. Thus, the tubular body has a wall that is a single layer formed by no more than two filaments stacked on top of one another.

Additional details about how the filaments are stacked on top of one another are disclosed below. Also, in the example of FIG. 5A, the filaments are always either on top of another filament or underneath a filament. The filaments never interweave with one another, so a filament is never on top of another filament in one position and then under the same filament at a different position.

Also, in FIG. 5A, the closed diamond-shaped cell formed by the helical filaments is elongated in the circumferential direction such that the distance from peak to peak or valley in the circumferential direction is longer than the distance from peak to peak or valley in the longitudinal direction. In the collapsed configuration, this changes so that the peak to peak or valley distance in the longitudinal direction is greater than the peak to peak or valley distance in the circumferential direction. Additionally, the angle formed by the crossing filaments is greater in the expanded configuration and smaller in the collapsed configuration. The filaments may cross one another so that a slightly raised thickness exists at the crossing point of two filaments while the portion of the filaments that do not cross are in the same circumferential plane as the other filaments, or slightly raised in a second plane as will be disclosed in greater detail below. Of course, one of skill in the art will appreciate that any number of open or closed cell geometries may be used and therefore diamond-shaped cells are not required or limiting in this or any of the examples disclosed herein. Other examples of cells may be square, rectangular, oval, elliptical, combinations thereof, or any other shape, and the filaments may also have any configuration including but not limited to linear, curved, undulating, combinations thereof, or any other shape.

FIG. 5B shows the tubular body of FIG. 5A in the collapsed configuration.

Figure 5C:
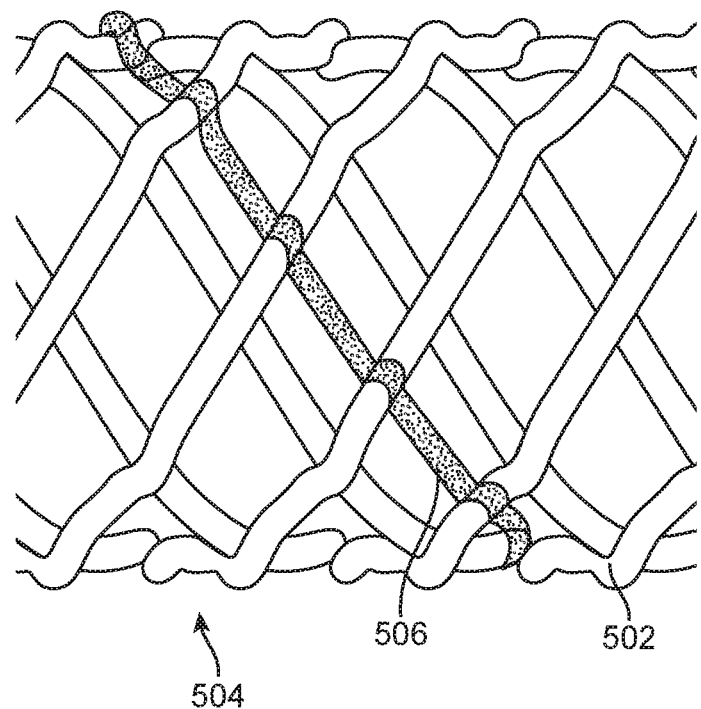
FIG. 5C shows a side view of a radially expandable member with an additional helical filament added to the example of FIG. 5A.

FIG. 5C illustrates how an additional filament 506 may be added to the example of FIGS. 5A-5B. Here, the additional filament 506 (highlighted in a darker line) remains disposed on top of each filament that it crosses and the point where two filaments crosses is slightly deformed so that the portion of the filament that does not cross another filament is in the same circumferential plane as the other filaments. The portion of the filament that crosses another filament may be slightly raised or other configurations are possible as will be discussed below. In this example, the tubular body is formed from an inner-most layer of filaments, a middle layer of filaments, and an outer-most layer of filaments. Therefore, the tubular body has a wall that is a single layer formed by no more than three filaments stacked on top of one another. Additionally, the inner-most layer of filaments maybe aligned in one helical direction, the middle layer transverse to the inner-most helical direction, and the outer-most layer of filaments transverse to the middle helical direction (or substantially parallel to the inner-most helical direction).

Figure 5D:
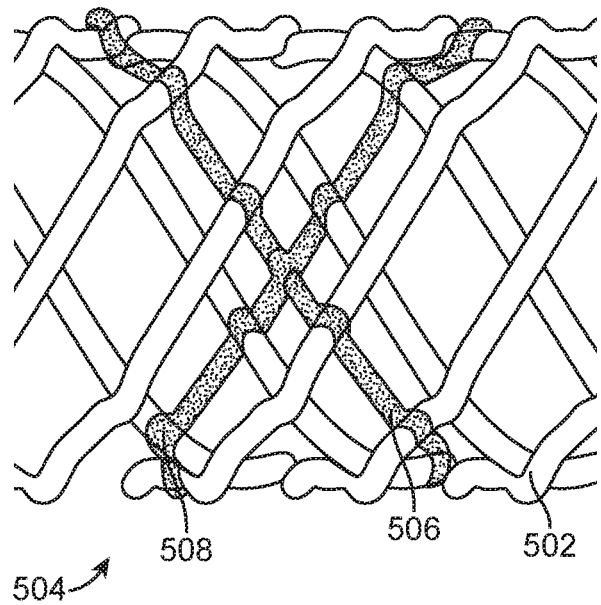
FIG. 5D shows a side view of a radially expandable member with an additional helical filament added to the example of FIG. 5C.

FIG. 5D adds yet another layer of filaments 508 to the example in FIG. 5C so now there are four layers of filaments that only cross one another so only two filaments are coupled together at any crossing point. And in this example, there is an inner-most layer of filaments, an inner middle layer of filaments, and outer middle layer of filaments, and an outer-most layer of filaments. Again, the filaments may alter their helical orientation from layer to layer so that one layer is transverse to the adjacent layer. The filaments maybe stacked on top of one another in any manner such as previously described above, or in any of the stacking examples described below.

Regardless of how many additional wires are superimposed, the sections of the wires between superimposed cross-sections result in a single layer of helical wires adjacent to the tissue, or bodily lumen (vessel, airway). Regardless of how many superimposed cross-sections of helical wires are present, the superimposed sections are directed toward the vessel wall or the airway wall. Each superimposed cross-section of helical wire may have a separate semi-flexible joint as discussed below.

Figure 6A:
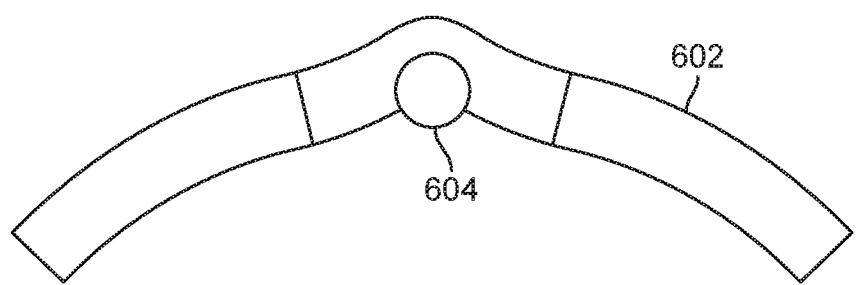
FIGS. 6A-6C illustrate examples of overlapping filaments.
Figure 6B:
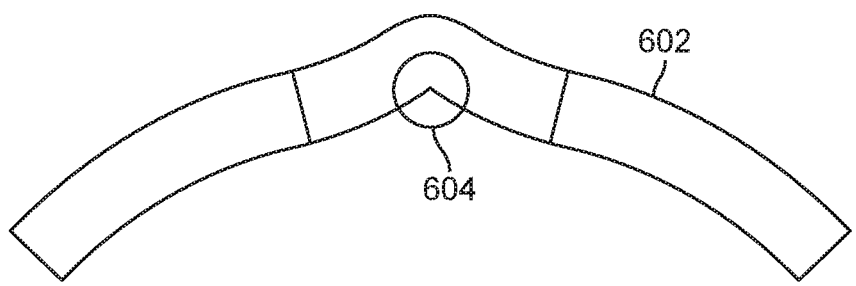
Figure 6C:
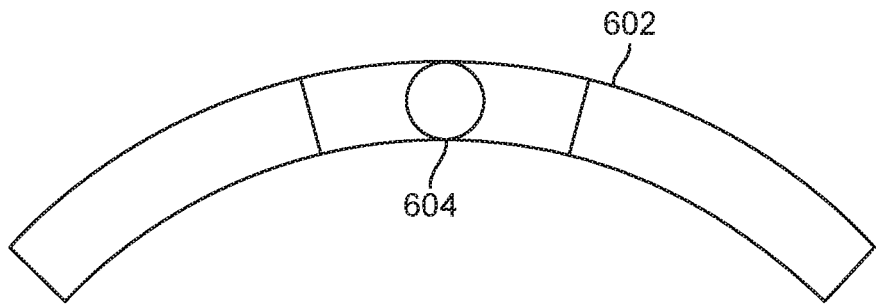

FIGS. 6A-6C illustrate various examples of how the filaments may cross an adjacent filament and this may be used in any of the examples of radially expandable devices disclosed herein.

FIG. 6A illustrates an example of two filaments 602, 604 that cross one another in any of the examples of radially expandable devices disclosed herein. The lower filament 604 is shown with a circular cross section that is undeformed. The upper filament 602 is shown crossing the lower filament such that the upper filament is slightly deformed around the lower filament to keep the total thickness of both filaments less than equal to the thickness of both filaments combined. Similarly, the thickness of the wall of the tubular body formed by both filaments will have a thickness that is also less than or equal to the thickness of both filaments combined. The filaments 602, 604 may be coupled to one another at the crossing point without any joint formed between the filaments, or the filaments may be joined together with a weld, adhesive, solvent bonded, or using any other techniques known in the art to form a joint. The joint may be rigid or resilient as will be discussed in greater detail below.

FIG. 6B shows the same filaments 602, 604 as in FIG. 6A overlapping one another to form a crossing point which may be used in any example of tubular body herein. However, in this example, the lower filament 604 is partially fused with the upper filament 602 to form the joint. The joint may be formed by welding, solvent bonding, etc. In this example, the thickness of the crossing point will be less than or equal to the combined thickness of both filament and greater than the thickness of either filament alone. By fusing the filaments together, the overall thickness of the tubular body will have a lower profile than if the filaments are simply stacked on top of one another. The resulting joint may be rigid or resilient as will be described below.

FIG. 6C shows another example of the crossing point formed by two filaments 602, 604 overlapping one another and which may be used in any tubular body example herein. Here, the two filaments are fully fused together so that the thickness of the joint or crossing point is less than or equal to the thickness of the upper filament 602. Again, the fusing maybe accomplished by any technique known in the art including welding, solvent bonding, etc. This configuration results in the lowest profile of the crossing point and the joint may be rigid, flexible or semi-flexible as discussed below.

In any of the examples shown in FIGS. 6A-6C, the filaments may have a round cross-section or any other cross-sectional shape including square, rectangular, elliptical, oval, etc. Additionally, as mentioned, the resulting joint between overlapping filaments may be a rigid joint or it may be a resilient joint that is fully or semi-flexible and configured to move as the tubular body is expanded and collapsed while still constraining axial movement of the filaments relative to one another. Thus, the filaments can pivot or rotate relative to one another but they do not linearly slide relative to one another. The thickness of the semi-flexible joint can range from the diameter or thickness of a single filament $d_1$, or superimposed filament $d_2$ and the sum of the two filaments $d_1+d_2$. The filaments may all have the same cross-section and thus same diameter or thickness, or they may be different. Similarly, they may be the same material, or different materials or hybrid materials. Examples of metallic materials that may be used for the filaments include but are not limited to stainless steel and metal alloys of nickel and titanium (e.g. nitinol materials). The filaments maybe formed with polymeric materials such as synthetic polymers, e.g. polyethylene terephthalate, polyamide, polyurethane, bioresorbable polymers such as polylactic acid (PLA), polyglycolic acid (PGA), polycaprolactone (PCL), polyanhydrides, poly(β-hydroxybutyrate), polydioxanone, poly(DTH iminocarbonate), polypropylene fumarate, etc. as well as copolymers thereof and mixtures thereof. In the hybrid device, both basic materials (metallic and polymeric) may be present in any proportion.

One filament cross-sectional size may be larger than another filament cross-sectional size, or smaller. Filament thickness may be determined based on design considerations such as radial strength and profile of the device in operation.

The expandable tubular body may have one joint or more than one joint. And the joints may be all resilient joints, all rigid joints, or combinations of resilient and rigid joints.

Figure 7A:
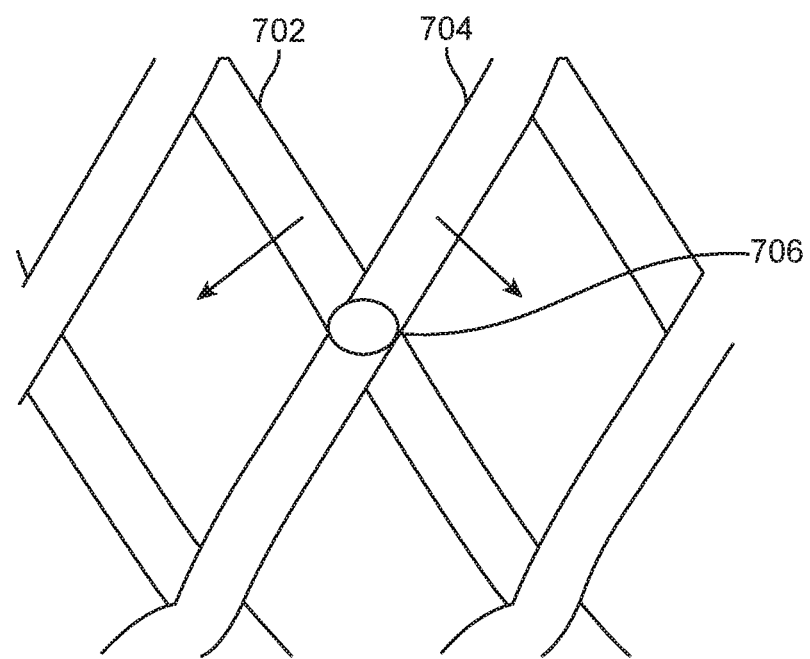
FIG. 7A illustrates an example of a resilient joint formed between filaments.

FIG. 7A shows the filaments forming a series of diamond shaped cells and the crossing point of two filaments 702, 704 which may be any filament described herein forming a joint 706 between the filaments. As disclosed above, this example and any other examples disclosed herein are not limited to diamond shaped cells. The cells may be open or closed, and may have any number of shapes including but not limited to rectangular, square, oval, elliptical, combinations thereof, or any shape. As previously discussed, the joint 706 may be simply the two filaments crossing and touching one another but unattached to one another, or the filaments may be attached to one another either fully fused together or partially fused together. The resulting joint may be rigid and inflexible, or the joint may be resilient and semi-flexible or fully flexible while maintaining the coupling of the overlapping filaments together. By joining the filaments together, the filaments are at least partially or fully constrained from sliding relative to one another thereby providing greater radial strength to the tubular body in the expanded configuration. A flexible or semi-flexible joint also allows the filaments to rotate or pivot relative to one another during expansion or collapse to reduce collapsed profile and still maintain radial strength as well as reducing the force required to radially expand the tubular body. FIG. 7A also shows how filaments 702 and 704 move away from one another as indicated by the arrows during collapsing of the tubular body. Therefore, the angle between the filaments will increase. The angle may be any angle between the filaments, but in this example may be the angle formed between adjacent filaments at a circumferentially oriented peak or valley of a closed cell. During expansion of the device, the filaments will move toward one another (in the opposite direction of the arrows) and the angle between filaments will decrease. The angle between adjacent filaments may move between 0 degrees and 90 degrees during expansion and collapse of the device. Similarly, for the angle formed between adjacent struts forming a peak or valley in the longitudinal direction, the angle decreases during collapsing and increases during radial expansion. Thus, a flexible or semi-flexible joint provides more desirable mechanical properties to the device as compared to an example where the filaments are woven together such that one filament passes on top of another filament and then goes under the next filament allowing the filaments to slide relative to one another during expansion and contraction as discussed below with reference to FIG. 7B.

Figure 7B:
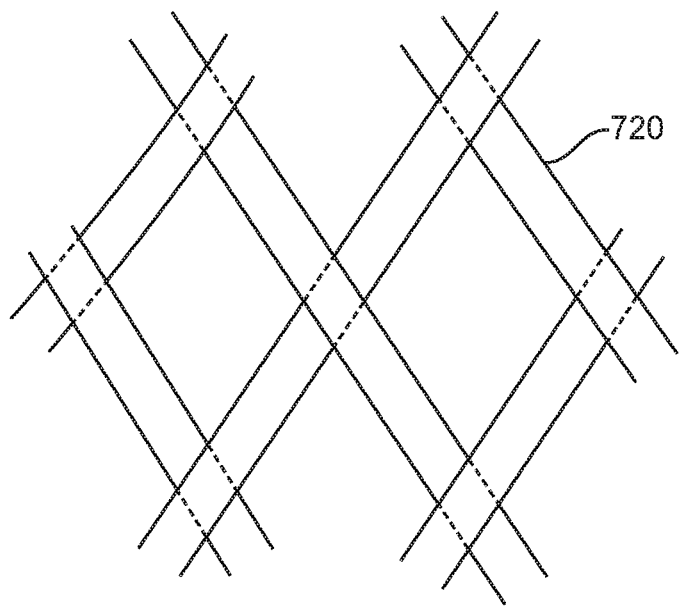
FIG. 7B shows woven filaments forming an expandable tubular body.

FIG. 7B shows an example where the filaments 720 are woven with one another so that a filament is disposed under one filament and then disposed over the adjacent filament in a repeating pattern. This may not provide as much radial strength as the joints described above in FIG. 7A because the filaments are unconstrained and free to slide relative to one another during expansion and collapsing of the device. Additionally, the profile of the device will be larger due to the overlapping filaments.

Figure 7C:
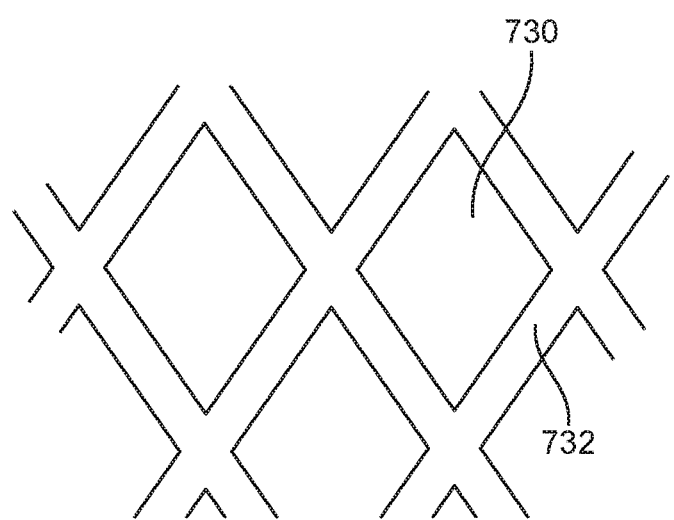
FIG. 7C shows integrally connected struts forming an expandable tubular body.

FIG. 7C shows a radially expandable tubular member that is formed from a plurality of slots 730 cut from a tube such as hypotube. The slots expand into diamonds during radially expansion and the slots flatten out during collapsing. Because the struts 732 are integral with one another this configuration provides radial strength but may require greater expansion forces to move the struts during expansion since there is no flexible or semi-flexible joint as seen with the superimposed helical filament examples disclosed herein, and the material around the joints must bend either elastically or plastically. This also makes it harder to uniformly collapse the tubular body once it is radially expanded, and repeated expansion and collapsing may fatigue and break the struts. Thus, the example of FIG. 7A provides many of the advantages of both the woven configuration of FIG. 7B and the integral strut or filament design of FIG. 7C, thereby providing relatively easy expansion and collapsing as well as good radial strength.

Figure 8A:
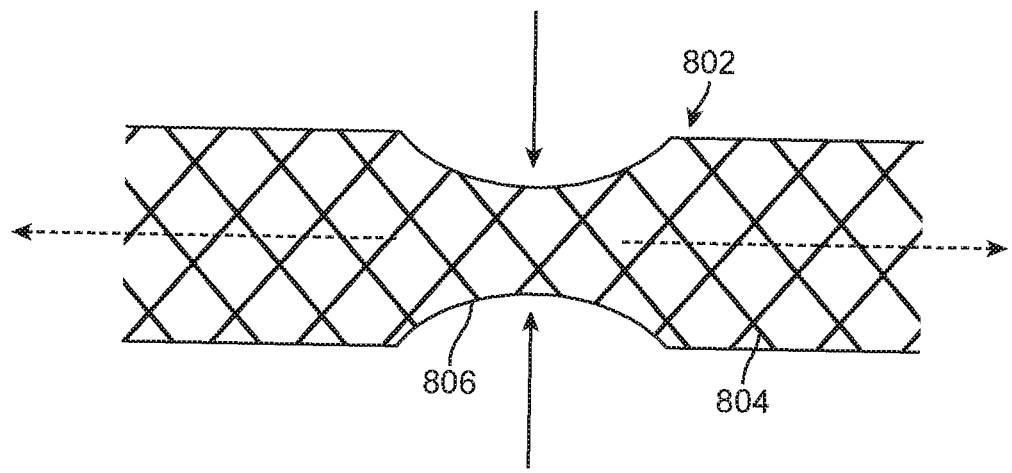
FIG. 8A illustrates a side view of compression of an expandable tubular body due to inadequate radial strength.
Figure 8B:
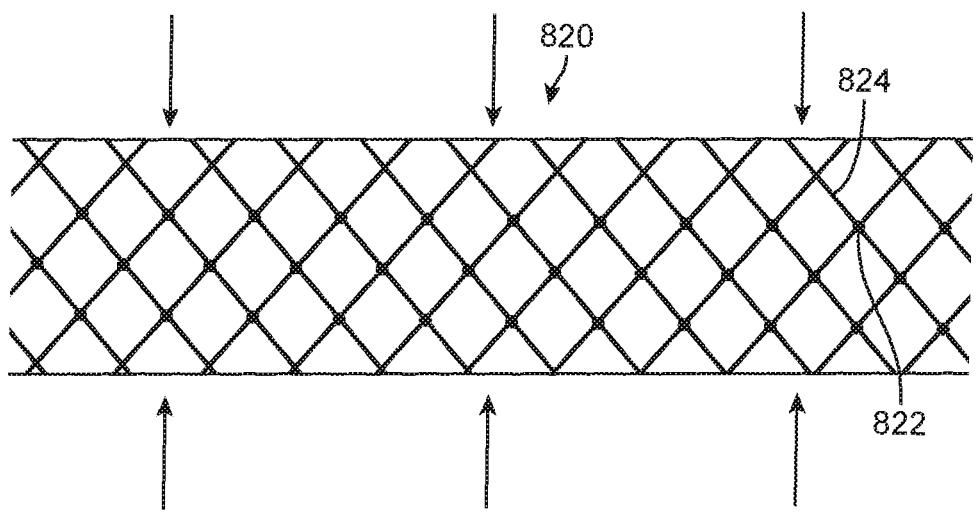
FIG. 8B illustrates a side view of uniform radial strength of an expandable tubular body.

FIG. 8A shows a typical woven design for a radially expandable member 802 where the wires extend under one adjacent wire and over another adjacent wire such as previously described in FIG. 7B above, and will be compared to the superimposed helical filament design in FIG. 8B which includes joints between the overlapping filaments. FIG. 8B provides some advantages over FIG. 8A.

In FIG. 8A the wires 804 are free to move relative to one another and thus radial strength in the expanded configuration may be reduced and the expanded tubular body may not have adequate radial strength. When a force as indicated by the inwardly pointing arrows is applied to the device, if the radial strength of the tubular body is not strong enough, the body will collapse 806 radially inward either at a discrete location or all along the tubular body, depending on how the force is applied to the tubular body. If the tubular body collapses it will not provide adequate support to the tissue and may not remain in apposition with the tissue thereby preventing or hindering therapeutic agent to be delivered to the tissue.

FIG. 8B shows a force (as indicated by the apposed arrows) applied to a tubular body 820 with adequate radial strength. Because the radial strength is greater than the force applied to the tubular body, the tubular body does not collapse and maintains its shape and continues to support and engage the tissue. The helical filaments 824 and the flexible or semi-flexible joints 822 allow the device to have uniform radial strength along its longitudinal axis, and that is greater than a traditionally woven tubular body. The tubular body 820 in FIG. 8B may be any of examples of superimposed helical filament examples disclosed herein.

FIGS. 9A-9D illustrate various geometries of radially expandable tubular bodies that may be formed using the helical filament construction described above. An optional guidewire is shown extending from the distal tip of the device.

Figure 9A:
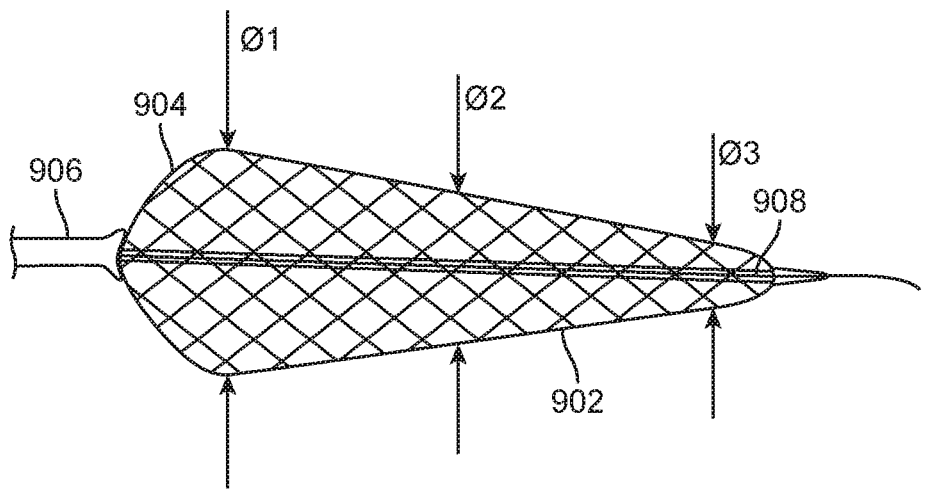
FIGS. 9A-9D illustrate side views of various examples of expanded radial tubular bodies.

FIG. 9A shows a radially expandable tubular body 902 that tapers from the proximal end to the distal end. Diameter $\ominus_1$ is greater than diameter $\ominus_2$ which is greater than diameter $\ominus_3$. Therefore, a brief shoulder 904 is coupled to the outer shaft 906 and then the maximum diameter is shown at the proximal end of the tubular body and the diameter tapers gradually down to the minimum diameter at the distal end which is coupled to the inner shaft 908. Tapering allows the radially expandable body to conform with the walls of a body channel such as a vascular lumen that has a similar taper in the proximal to distal direction. Actuation of the tubular body functions generally the same way as previously described above in FIGS. 3A-3B.

Figure 9B:
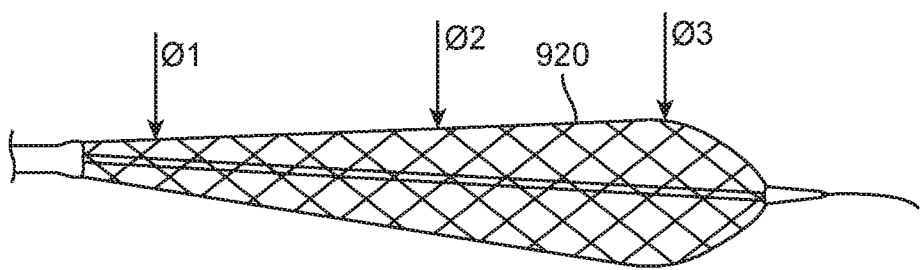

FIG. 9B shows an example similar to FIG. 9A with the major difference being that the taper is reversed and therefor the maximum diameter is near the distal end of the tubular body and this tapers proximally to the small diameter on the proximal end, thus the tubular body 920 has a diameter $\ominus_1$ that is smaller than diameter $\ominus_2$ which is smaller than diameter $\ominus_3$. Again, this taper allows the expandable member to conform to the walls of a body channel such as a vascular lumen that has a similar taper in the distal to proximal direction. This example may also be described as having a distal flared tubular body.

Figure 9C:
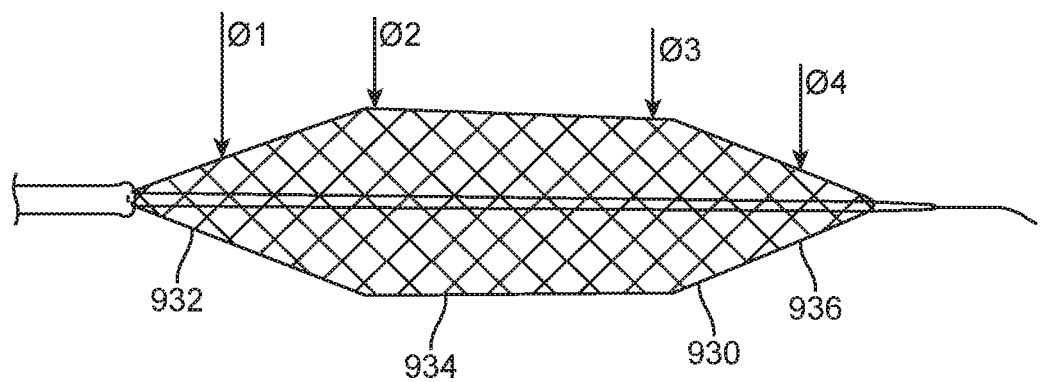

FIG. 9C shows an expandable member 930 having a flared proximal 932 end with increasing diameter, then a constant diameter mid-section 934 that then transitions into a distally tapering region 936. Thus, proximal diameter $\ominus_1$ is smaller than diameter $\ominus_2$ which is the same as diameter $\ominus_3$ which is greater than $\ominus_4$. The constant diameter mid-section 934 may be the working portion that is used to support tissue and the flared and tapered should sections 932, 936 may not support or engage tissue. Or the body channel may have walls which match this shape and are supported by some or all sections of the flared, constant diameter or tapered sections.

Figure 9D:
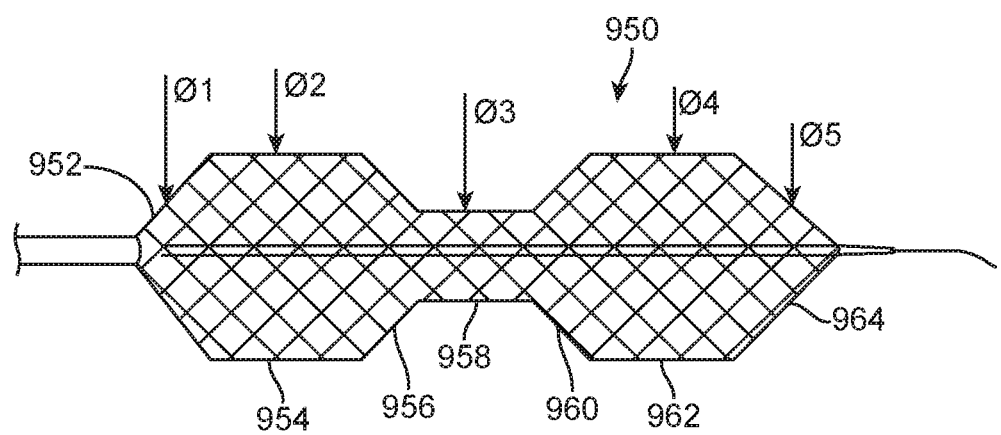

FIG. 9D shows still another example of an expandable tubular body 950 that may be formed from any of the helical filament examples disclosed herein. In this example, the tubular body is formed from helical filaments with any of the joints described herein. A proximal section has a flared region 952, then the tubular body has a constant diameter section 954 followed by a taper 956 that tapers distally to a center section 958 that has a constant diameter. The constant diameter center section then flares outward 960 again increasing in diameter to another constant diameter section 962, followed by a distally tapering section 964. Again, any shape may be formed in order to support the target treatment tissue. Thus, diameter $\ominus_1$ is smaller than diameter $\ominus_2$ which is larger than diameter $\ominus_3$ which is smaller than diameter $\ominus_4$ which is larger than diameter $\ominus_5$.

Figure 10:
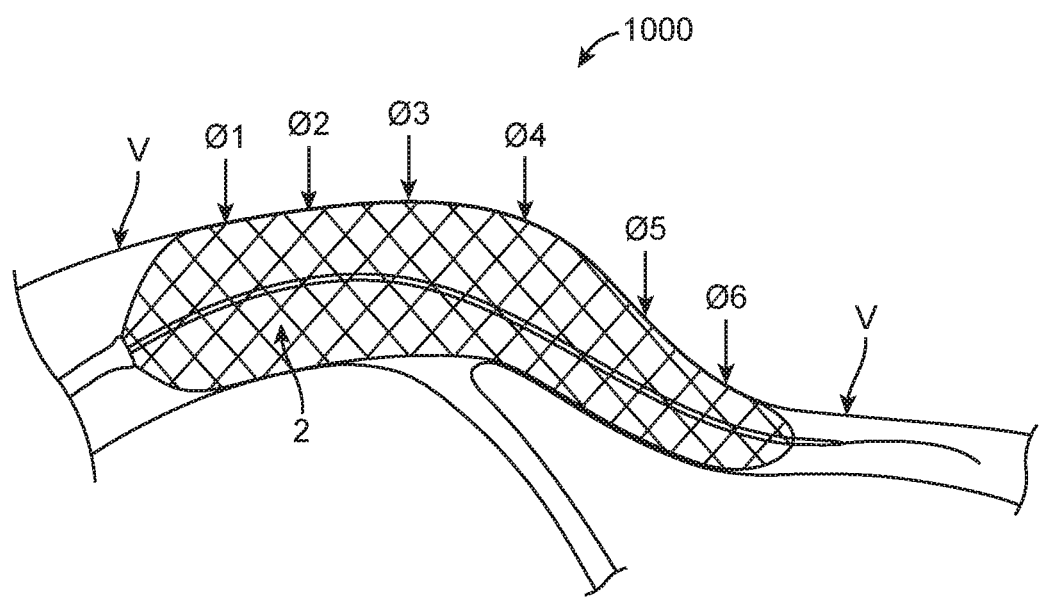
FIG. 10 illustrates a side view of an example of an expanded radial tubular body with varying diameter.

FIG. 10 shows how a superimposed helical filament design 1000 such as any of those disclosed herein may be used to provide a personalized design that adapts to the local anatomy. Because the filaments may have a resilient joint coupling overlapping filaments, the outer diameter of the expanded tubular body may expanded until it engages the treatment tissue, here a blood vessel V, and thus the expanded tubular body will conform to the contours of the treatment region so that diameter and curvature of the tubular body may vary along its length. Thus, diameters $\ominus_1$, $\ominus_2$, $\ominus_3$, $\ominus_4$, $\ominus_5$, and $\ominus_6$ may be the same, may be different than one another or some may be the same and some different depending on the diameter of the vessel V. This customized expandable device therefore adapts to the anatomy based on medical information and imaging such as angiograms, computerized tomography (CT), computerized tomography angiography (CTA), magnetic resonance imaging (MRI), magnetic resonance angiography (MRA), ultrasound, x-ray, optical coherence tomography (OCT), intravascular ultrasound (IVUS), as well as any other imaging modality known in the art, and provides a variable diameter tubular body that conforms to a vessel wall or any other tissue wall. Here the proximal end of the tubular body flares outward with increasing diameter to a maximum diameter section which then gradually tapers distally to the distal end. The tubular body is expanded and in engagement with the walls of a vessel to support the vessel and/or elute a therapeutic agent to the tissue that engages the tubular body. In addition, the diameter of the device conforms to the walls of the treatment site, the longitudinal axis of the device also conforms to the curvature of the channel, vessel or other body cavity. A drug may be delivered from the expandable tubular body and/or the device may simply provide temporary support to the walls of the tissue until they can remodel and remain patent. The helical filament construction with flexible or semi-flexible joints also allows the tubular body to provide a uniform radial outward force on the tissue even though the diameter varies.

Figure 11A:
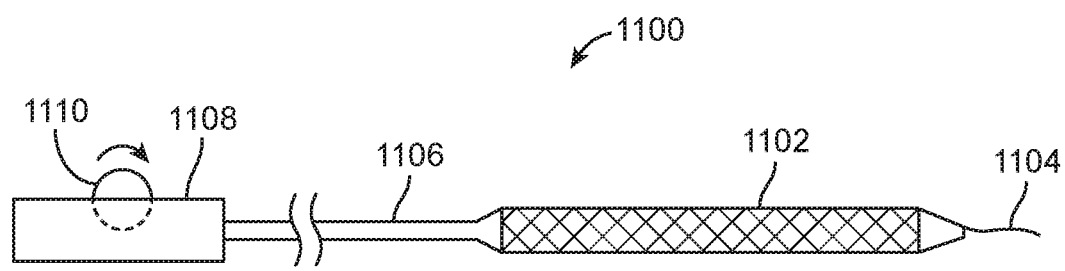
FIG. 11A illustrates a side view of an example of a handle for actuating the radially expandable member.

FIG. 11A shows an example of a support device 1100 having an expandable tubular body 1102 which may be any of those disclosed herein formed with any of the helical filament examples herein and having any of the filament joints disclosed herein. Optional guidewire 1104 extends past the distal end of the catheter. Inner and outer shafts 1106 (only the outer shaft is visible in this view) are coupled to the expandable member 1102 as described previously and are used to expand and collapse the radially expandable member. The proximal ends of the inner and outer shafts are operatively coupled to a handle 1108 that is ergonomically shaped to allow an operator to grasp and manipulate the handle. The handle may include an actuator 1110 such as a slide, lever, rotatable wheel or other actuation element that is operatively coupled to the inner and outer shafts such that actuation of the actuator in one direction will move the inner and outer shafts relative to one another to radially expand the tubular body, while actuation of the actuator in the opposite direction will move the inner and outer shafts in an opposite direction relative to one another thereby collapsing the radially expandable member. The handle may also include a gage or other visual indicia (not shown) to show the operator the diameter of the expandable tubular body. An optional guidewire 1104 is shown slidably disposed in the device.

Figure 11B:
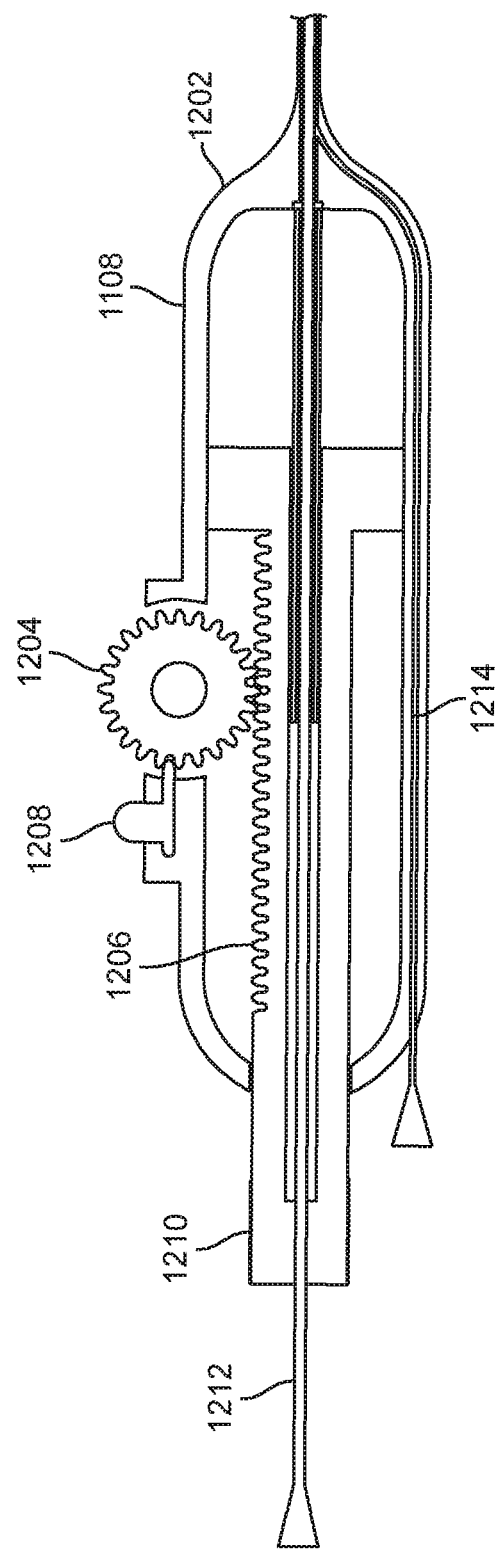
FIG. 11B illustrates a side view of an example of an actuator in a handle.

FIG. 11B shows an example of a handle 1108 which may be used in FIG. 11A or with any of the examples disclosed herein. Handle 1108 includes a housing 1202 which is ergonomically shaped to fit in an operator's hand and houses at least some of the actuator components including an actuator wheel 1204, a rack 1206, and a locking element 1208. The inner shaft 1212 may be coupled to a plunger 1210 that is coupled to the rack 1206. The rack includes a number of teeth that engage with the teeth on actuator wheel 1204. Thus, as actuator wheel 1204 is rotated in one direction, the rack will move in one direction and the inner shaft will therefore also move in one direction. When the actuator wheel is rotated in a second opposite direction, the rack will move in a second opposite direction thereby causing the inner shaft to move in a second opposite direction.

FIG. 11C shows the handle of FIG. 11B coupled to an expandable member 1218 which may be any of those described herein. The outer shaft 1216 is fixed to the handle, thus resulting in relative movement between the inner and outer shafts which can therefore expand or collapse the expandable member 1218. The wheel may be actuated multiple times back and forth to expand and collapse the expandable member as needed. The inner shaft may extend to the proximal end of the handle where a valve, Luer connector or other connector may be coupled to the proximal end of the inner shaft to prevent fluid from flowing past the proximal end. A guidewire (not illustrated in this figure) may be inserted into a lumen of the inner shaft and extend all the way through the inner shaft lumen and exit at the distal end of the device as shown in previous figures, and the lumen may also be flushed with a fluid to remove air or other unwanted fluids or gases. As indicated earlier, the outer shaft is fixed to the handle and therefore is stationary in this example. The annular gap between the inner and outer shafts may also be flushed with a second path 1214 that is fluidly coupled to the annular gap. The proximal end of pathway 1214 may also have a Luer connector, stopcock, or any other connector as needed to control fluid flow.

As the radially expandable member is expanded or collapsed, it may be desired to lock the diameter at a certain size and hold it at that size during a procedure. A lock 1208 may be included on the handle. The lock can be any number of locks such as a pawl that prevents movement of the actuator wheel unless the lock is unlocked.

FIG. 11D highlights a distal section of the handle in FIG. 11C and illustrates how the flush lumen 1214 is coupled to the annular space between the inner and outer shafts 1212, 1216.

And this example is not intended to be limiting. As discussed previously, relative movement of the inner and outer shafts is needed to expand and collapse the expandable member. Therefore, the outer shaft may be coupled to the rack and the inner shaft maybe fixed to the handle in another example. Other actuators are known in the art and may also be used. Levers, slides, or any other known actuators may be used instead of an actuator wheel. The actuator wheel or other actuator may also have indicia that indicate the diameter or size of the expandable member as it expands and collapses. For example, the actuator wheel may have a clicking noise to indicate size, or markings which show the diameter.

FIGS. 12A-12I illustrate various examples of actuator orientations relative to the handle that may be used in any example. The handle H is coupled to the inner and outer shafts as previously described above. An actuator, here a rotatable wheel W is shown coupled to the handle H.

Figure 12A:
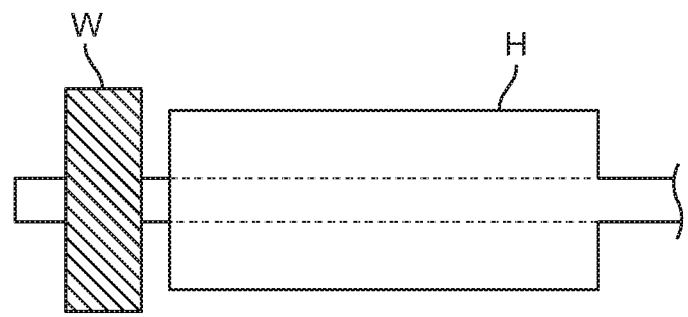
FIGS. 12A-12I illustrate side views of various actuator configurations on a handle.

In FIG. 12A, the wheel W is on a proximal end of the handle H and the wheel is transverse or orthogonal to the longitudinal axis of the handle. The wheel rotates around the longitudinal axis of the handle and inner/outer shafts.

Figure 12B:
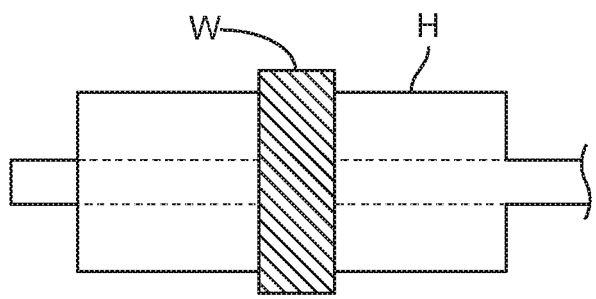

FIG. 12B shows a similar example as FIG. 12A with the major difference being that the wheel W has been moved so it is now disposed over a middle portion of the handle H but otherwise is substantially similar to the example in FIG. 12A.

Figure 12C:
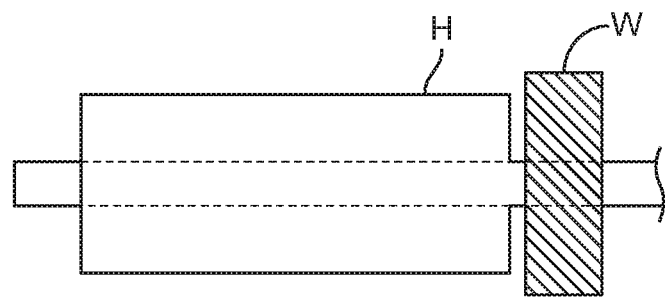

FIG. 12C shows a similar example as FIG. 12A with the major difference being that the wheel W has been moved so that it is now disposed at the proximal end of the handle H but otherwise is substantially similar to the example in FIG. 12A.

Figure 12D:
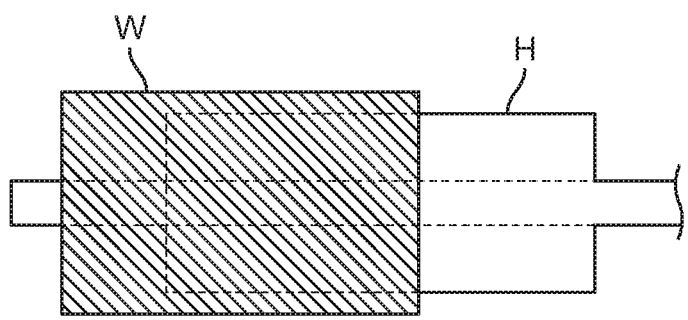

FIG. 12D illustrates an example where the handle H includes the rotatable wheel W. Here, a proximal portion of the handle is the rotatable wheel W and therefore as the handle is rotated in different directions, the handle will be drawn into or away from the rotatable wheel. The wheel may be concentric with the inner and outer shafts.

Figure 12E:
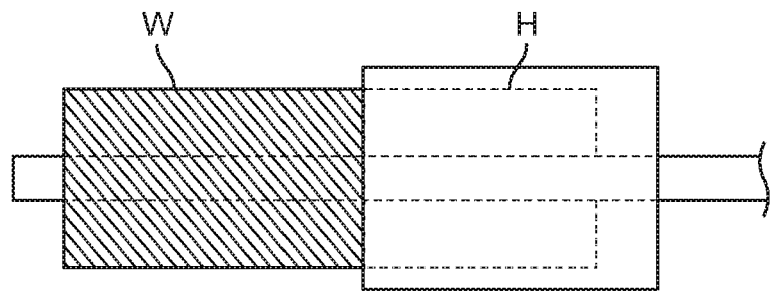

FIG. 12E is similar to the example of FIG. 12D with the major difference being that the handle body H has a larger size than the rotatable wheel. Rotation of the wheel will draw the wheel into or way from the handle. Rotation of the wheel is generally concentric to the longitudinal axis of the inner and outer shafts.

Figure 12F:
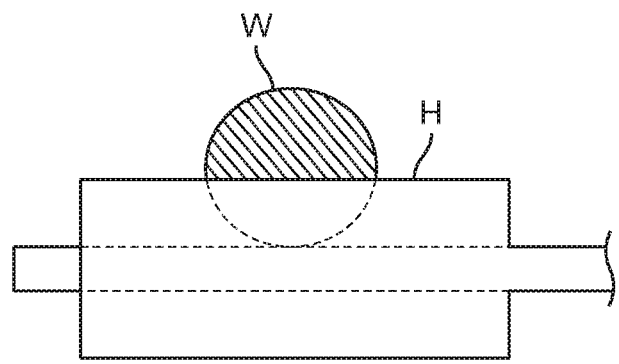

FIG. 12F shows the rotatable wheel W protruding from a top or bottom surface of the handle H. Approximately half of the wheel will be exposed while approximately the other half will be housed in the handle. The wheel may be located in the middle portion of the handle or anywhere on the handle and rotation of the wheel will generally be in the same parallel direction to the inner and outer shafts.

Figure 12G:
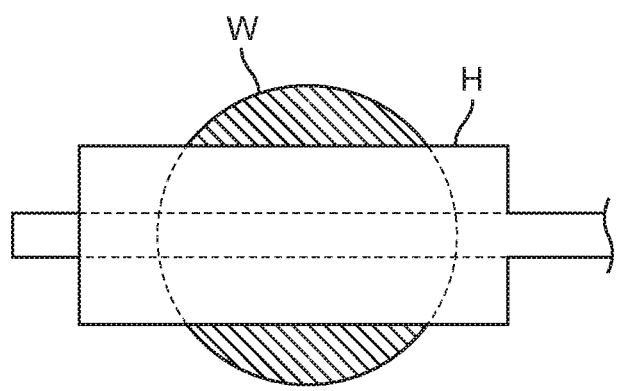

FIG. 12G shows another example of a wheel W that protrudes from the top and the bottom surfaces of the handle H. Therefore, the wheel may be actuated from either the top or bottom. Actuation is generally in the same direction as above in FIG. 12F.

Figure 12H:
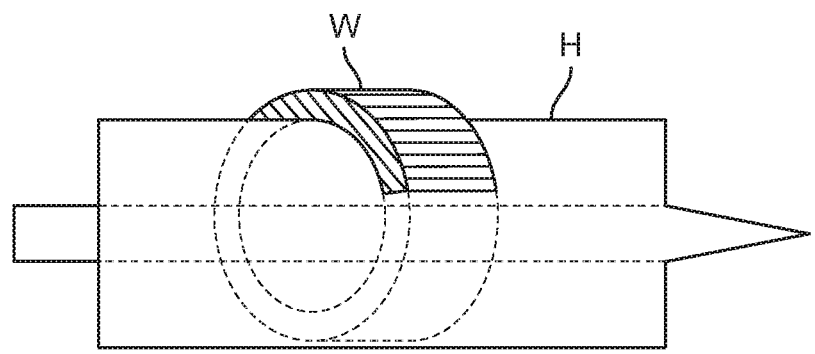

FIG. 12H shows another example of an actuator wheel W coupled to a handle H. Here the wheel W may be disposed outside the handle and is now canted relative to the handle and therefore the wheel rotates in a plane that is transverse or oblique to the longitudinal axis of the inner and outer shaft. Here, a left side of the wheel is canted proximally, while a right side of the wheel canted distally in this side view of the handle. The wheel may extend partially or completely around the handle to form a closed or open ring.

Figure 12I:
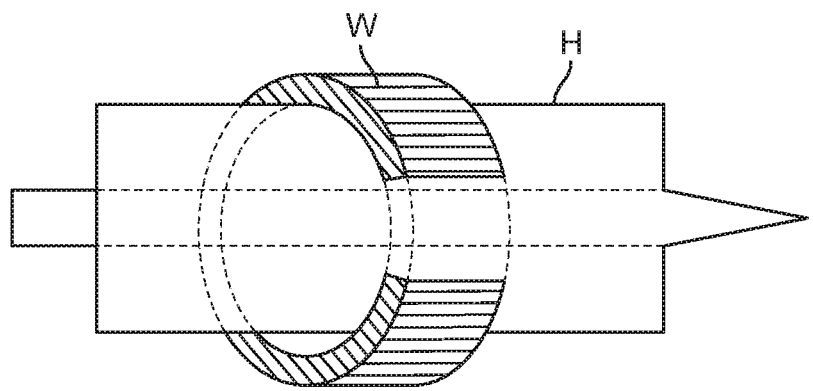

FIG. 12I is another example of a canted wheel W that is disposed around the outside of the handle H. Here the wheel will rotate in a plane that is transverse or oblique the longitudinal axis of the inner and outer shafts. In this example which is a side view of the handle, the top of the wheel is canted proximally and the bottom of the wheel is canted distally. The wheel may extend completely or partially around the handle to form a closed ring or an open ring.

Any example disclosed herein may include a therapeutic agent. The helical filaments or any portion of the device may be coated with a coating layer that contains a therapeutic agent or a mixture of therapeutic agents. The therapeutic agent may be carried by the helical filaments or any part of the device and may include paclitaxel, sirolimus also known as rapamycin, corticosteroids, nonsteroidal anti-inflammatory drugs, anticoagulants, etc. The therapeutic agent may be disposed in a coating coupled to the helical filaments such as a mixture of polymers and therapeutic agents. The polymers are drug carriers such as, polyvinyl alcohol, polyethylene glycol, polyvinyl polypyrrolidone, poly(L-lactide), polylysine, etc. The ratio of polymer to therapeutic agent may be any ratio but examples of this ratio may include: 1:9; 2:8; 3:7; 4:6, 5:5, 6:4 as well as any tenth of the ratio. For example, in a 1:9 ratio of polymer to therapeutic agent, the ratio may include any of 1.1; 1.2; 1.3; 1.4; 1.5; 1.6; 1.7; 1.8; or 1.9 to any of 9.1; 9.2; 9.3, 9.4; 9.5; 9.6; 9.7; 9.8; or 9.9.

In any example disclosed herein a fluid such as blood or any body fluid or any liquid, or a gas such as air is free to pass by the tubular body in the expanded or collapsed configuration because the tubular body has a lumen for fluid flow and the walls of the tubular body are porous. Additionally, the tubular body may be expanded and held in an expanded configuration for any length of time such as less than or equal to 30 seconds, or less than or equal to 30 minutes, or less than or equal to 60 minutes, or even longer than 60 minutes until a desired therapeutic effect is obtained. Desired therapeutic effects may include delivery of a therapeutic agent to the target treatment tissue or remodeling of the target treatment tissue so that it is self-supporting. Any of the examples of superimposed helical tubular bodies may be used to deliver therapeutic agents to a target treatment area. The therapeutic agent maybe delivered continuously over a short initial period of time, or during the entire time the device contacts the target treatment area. Moreover, the same device maybe used repeatably to expand and support one or different areas in the same patient as well as deliver a therapeutic agent in one or different areas in the same patient. Thus, any of the examples disclosed herein may be used to expand and collapse multiple times and be held in the expanded configuration for a desired time before being removed from the patient.

NOTES AND EXAMPLES

The following, non-limiting examples, detail certain aspects of the present subject matter to solve the challenges and provide the benefits discussed herein, among others.

Example 1 is a temporary and expandable tissue support device, the device comprising: a plurality of helical filaments superimposed on top of one another to form a tubular body having a first end, a second end opposite the first end, and a lumen extending between the first end and the second end; an inner shaft; and an outer shaft slidably disposed over the inner shaft, wherein the first end is coupled to the inner shaft, and the second end is coupled to the outer shaft, wherein actuation of the inner and outer shafts in a first direction compresses the plurality of filaments thereby radially expanding the tubular body into an expanded configuration that is adapted to engage and support tissue at a treatment site without obstructing a fluid from flowing past the tubular body, and wherein actuation of the inner and outer shafts in a second direction opposite the first direction tensions the plurality of filaments thereby radially collapsing the tubular body into a collapsed configuration that is adapted to be delivered to or removed from the treatment site.

Example 2 is the device of Example 1, wherein the tubular body comprises a sidewall with a plurality of apertures therethrough.

Example 3 is the device of any of Examples 1-2, wherein the plurality of helical filaments crosses one another at a plurality of crossing points, and wherein each crossing point comprises no more than two of the plurality of helical filaments.

Example 4 is the device of any of Examples 1-3, wherein the plurality of filaments is disposed in a single circumferentially oriented planar layer.

Example 5 is the device of any of Examples 1-4, wherein the plurality of helical filaments each have a thickness and the plurality of helical filaments cross one another at a plurality of crossing points, and wherein each crossing point has a thickness greater than or equal to the thickness of one of the plurality of filaments, and the thickness is less than or equal to the thickness of two of the plurality of filaments.

Example 6 is the device of any of Examples 1-5, wherein the plurality of helical filaments crosses one another at a plurality of crossing points, and wherein at least some of the plurality of crossing points comprises two of the plurality of helical filaments attached to one another with a resilient joint.

Example 7 is the device of any of Examples 1-6, wherein the resilient joint is configured to flex as the tubular body moves between the expanded configuration and the collapsed configuration.

Example 8 is the device of any of Examples 1-7, wherein the two helical filaments form a crossing angle at the crossing point, and wherein the crossing angle changes up to 90 degrees during movement between the expanded configuration and the collapsed configuration.

Example 9 is the device of any of Examples 1-8, wherein the plurality of helical filaments crosses one another at a plurality of crossing points, and wherein at least some of the plurality of crossing points comprises two of the plurality of helical filaments crossing one another without an attachment therebetween.

Example 10 is the device of any of Examples 1-9, further comprising a therapeutic agent carried by the tubular body, wherein the therapeutic agent is configured to be delivered therefrom to the tissue at the treatment site.

Example 11 is the device of any of Examples 1-10, wherein the therapeutic agent comprises an anti-restenosis, anti-inflammatory or anticoagulant agent.

Example 12 is the device of any of Examples 1-11, further comprising a handle coupled to a proximal end of the inner shaft and a proximal end of the outer shaft, the handle further comprising an actuator element, wherein actuation of the actuator element moves the inner shaft relative to the outer shaft to expand or collapse the tubular body.

Example 13 is the device of any of Examples 1-12, wherein the handle further comprises an indicator element configured to indicate to an operator a size of the tubular body.

Example 14 is the device of any of Examples 1-13, wherein the first end of the tubular body is coupled to the inner shaft asymmetrically or the second end of the tubular shaft is coupled to the outer shaft asymmetrically.

Example 15 is the device of any of Examples 1-14, wherein an outer diameter of the tubular body varies along a longitudinal axis of the tubular body.

Example 16 is the device of any of Examples 1-15, wherein a fluid or gas passes through or around the tubular body without restriction when the tubular body is in the expanded configuration or the collapsed configuration.

Example 17 is the device of any of Examples 1-16, wherein the tubular body in the expanded configuration applies a constant force to the tissue.

Example 18 is the device of any of Examples 1-17, wherein the tubular body has a first expanded configuration and a second expanded configuration, and wherein the first expanded configuration applies a force to the tissue, and wherein the second expanded configuration applies a second force greater than the first force to the tissue.

Example 19 is a method for temporarily supporting tissue at a treatment site in a patient, the method comprising: providing a tubular body formed from a plurality of helical filaments superimposed on top of one another, the tubular body comprising a first end, a second end opposite the first end and a lumen extending therebetween; advancing the tubular body in a collapsed configuration to the treatment site; actuating an inner shaft in a first direction relative to an outer shaft slidably disposed over the inner shaft, wherein the first end is coupled to the inner shaft, and the second end is coupled to the outer shaft thereby compressing the plurality of filaments and radially expanding the tubular body into an expanded configuration that engages and supports the tissue without obstructing a fluid or gas from flowing past the tissue; maintaining the tubular body in the expanded configuration for a predetermined amount of time and supporting the tissue; actuating the inner shaft in a second direction opposite the first direction relative to the outer shaft thereby tensioning the plurality of filaments and radially collapsing the tubular body into the collapsed configuration; and removing the inner shaft, the outer shaft, and the tubular body from the patient.

Example 20 is the method of Example 19, wherein the plurality of helical filaments crosses one another at a plurality of crossing points, and wherein each crossing point comprises no more than two of the plurality of helical filaments.

Example 21 is the method of any of Examples 19-20, wherein the plurality of helical filaments each have a thickness and the plurality of helical filaments cross one another at a plurality of crossing points, and wherein each crossing point has a thickness greater than or equal to the thickness of one of the plurality of filaments, and the thickness is less than or equal to the thickness of two of the plurality of filaments.

Example 22 is the method of any of Examples 19-21, wherein the plurality of helical filaments crosses one another at a plurality of crossing points, wherein each crossing point comprises two of the plurality of helical filaments attached to one another with a resilient joint, and wherein radially expanding or radially collapsing the tubular body comprises flexing the resilient joint.

Example 23 is the method of any of Examples 19-22, wherein the two helical filaments form a crossing angle at the crossing point, and wherein radially expanding or radially collapsing the tubular body comprises changing the crossing angle up to 90 degrees during movement between the expanded configuration and the collapsed configuration.

Example 24 is the method of any of Examples 19-23, wherein the tubular body further comprises a therapeutic agent, the method further comprising delivering the therapeutic agent to the tissue.

Example 25 is the method of any of Examples 19-24, wherein delivering the therapeutic agent comprises delivering the therapeutic agent continuously during the predetermined time that the tubular body is maintained in the expanded configuration.

Example 26 is the method of any of Examples 19-25, wherein the therapeutic agent comprises an anti-restenosis, anti-inflammatory or anticoagulant agent.

Example 27 is the method of any of Examples 19-26, further comprising a handle coupled to a proximal end of the inner shaft and a proximal end of the outer shaft, the handle further comprising an actuator, the method further comprising actuating the actuator thereby moving the inner shaft relative to the outer shaft and expanding or collapsing the tubular body.

Example 28 is the method of any of Examples 19-27, further comprising displaying a size of the tubular body with an indicator element on the handle as the actuator is being actuated.

Example 29 is the method of any of Examples 19-28, wherein the first end of the tubular body is coupled to the inner shaft asymmetrically or the second end of the tubular shaft is coupled to the outer shaft asymmetrically.

Example 30 is the method of any of Examples 19-29, wherein radially expanding the tubular body comprises radially expanding the tubular body so that an outer diameter of the tubular body varies along a longitudinal axis of the tubular body.

Example 31 is the method of any of Examples 19-30, wherein the outer diameter is personalized to match contours of the treatment site in the patient.

Example 32 is the method of any of Examples 19-31, further comprising adjusting a position of the tubular body to a new location along the treatment site before removing the tubular body from the patient.

Example 33 is the method of any of Examples 19-32, further comprising permitting a fluid to pass the tubular body without restriction when the tubular body is in the expanded configuration or the collapsed configuration.

Example 34 is the method of any of Examples 19-33, wherein maintaining the tubular body in the expanded configuration applies a constant force to the tissue.

Example 35 is the method of any of Examples 19-34, wherein maintaining the tubular body in the expanded configuration comprises increasing an applied force to the tissue over a desired period of time.

Example 36 is the method of any of Examples 19-35, wherein maintaining the tubular body in the expanded configuration comprises supporting the tissue until the tissue remodels to a desired status.

Example 37 is the method of any of Examples 19-36, wherein actuating the inner shaft in the first direction comprises actuating the inner shaft in the first direction a plurality of times and radially expanding the tubular body into the expanded configuration a plurality of times.

Example 38 is the method of any of Examples 19-37, wherein actuating the inner shaft in the second direction comprises actuating the inner shaft in the second direction a plurality of times and radially collapsing the tubular body into the collapsed configuration a plurality of times.

In Example 39, the apparatuses or methods of any one or any combination of Examples 1-38 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A temporary and expandable tissue support device, the device comprising:
    a plurality of superimposed helical filaments forming an inner layer of filaments and an outer layer of filaments, wherein the outer layer of filaments remains disposed on top of the inner layer of filaments and the inner layer of filaments remains disposed underneath the outer layer of filaments, without interweaving of the inner and outer layers of filaments, the inner layer of filaments and the outer layer of filaments forming a tubular body having a first end, a second end opposite the first end, and a lumen extending between the first end and the second end, wherein at least some of the plurality of filaments in the inner layer are fused with at least some of the plurality of filaments in the outer layer to form resilient joints that are flexible and move as the tubular body is expanded or collapsed while preventing sliding of the fused filaments relative to one another, and wherein each of the plurality of filaments has a thickness and wherein the resilient joints have a thickness that is greater than or equal to the thickness of one of the plurality of filaments, and wherein the resilient joints have a thickness that is less than the thickness of two of the plurality of filaments;
    an inner shaft; and
    an outer shaft slidably disposed over the inner shaft, wherein the first end is coupled to the inner shaft, and the second end is coupled to the outer shaft,
    wherein actuation of the inner shaft or outer shaft relative to the other of the inner shaft or the outer shaft in a first direction compresses the plurality of filaments thereby radially expanding the tubular body into an expanded configuration that is adapted to engage and support tissue at a treatment site without obstructing a fluid from flowing past the tubular body, and
    wherein actuation of the inner or outer shaft relative to the other of the inner shaft or outer shaft in a second direction opposite the first direction tensions the plurality of filaments thereby radially collapsing the tubular body into a collapsed configuration that is adapted to be delivered to or removed from the treatment site.

2. The device of claim 1, wherein the plurality of helical filaments crosses one another at a plurality of crossing points, and wherein each crossing point comprises no more than two of the plurality of helical filaments.

3. The device of claim 1, wherein the plurality of helical filaments is disposed in a single circumferentially oriented planar layer.

4. The device of claim 1, wherein one or more of the resilient joints is formed with two of the plurality of helical filaments and the two helical filaments form a crossing angle at the crossing point, and wherein the crossing angle changes up to 90 degrees during movement between the expanded configuration and the collapsed configuration.

5. The device of claim 1, further comprising a handle coupled to a proximal end of the inner shaft and a proximal end of the outer shaft, the handle further comprising an actuator element, wherein actuation of the actuator element moves the inner shaft relative to the outer shaft to expand or collapse the tubular body.

6. The device of claim 1, wherein a fluid or a gas passes through or around the tubular body without restriction when the tubular body is in the expanded configuration or the collapsed configuration.

7. The device of claim 1, wherein the tubular body in the expanded configuration applies a constant force to the tissue.

8. The device of claim 1, wherein the tubular body has a first expanded configuration and a second expanded configuration, and wherein the first expanded configuration applies a force to the tissue, and wherein the second expanded configuration applies a second force greater than the first force to the tissue.

* * * * *

UNITED STATES PATENT AND TRADEMARK OFFICE
CERTIFICATE OF CORRECTION

| | | |
|---|---|---|
| PATENT NO. | : 11,090,174 B1 | Page 1 of 1 |
| APPLICATION NO. | : 16/787573 | |
| DATED | : August 17, 2021 | |
| INVENTOR(S) | : Nikanorov et al. | |

It is certified that error appears in the above-identified patent and that said Letters Patent is hereby corrected as shown below:

On the Title Page

Item (22), in Column 1, Line 1, after "2020", insert --¶(65) Prior Publication Data
US 2021/0244551 A1 Aug. 12, 2021--

Item (56) On page 2, in Column 1, under "Other Publications", Line 2, delete "2012"," and insert
--2021",-- therefor Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*